(12) United States Patent
Hauck et al.

(10) Patent No.: US 7,996,055 B2
(45) Date of Patent: Aug. 9, 2011

(54) CARDIAC NAVIGATION SYSTEM INCLUDING ELECTRODE ARRAY FOR USE THEREWITH

(75) Inventors: John A. Hauck, Shoreview, MN (US); James C Baker, Woodbury, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1257 days.

(21) Appl. No.: 11/618,676

(22) Filed: Dec. 29, 2006

(65) Prior Publication Data

US 2008/0161669 A1   Jul. 3, 2008

(51) Int. Cl.
*A61B 5/0402* (2006.01)
(52) U.S. Cl. .......... 600/374; 600/393; 600/509
(58) Field of Classification Search .......... 600/374, 600/386, 388–390, 393, 509
See application file for complete search history.

(56) References Cited

U.S. PATENT DOCUMENTS

| | | | |
|---|---|---|---|
| 5,297,549 A | 3/1994 | Beatty et al. | |
| 5,553,611 A | 9/1996 | Budd et al. | |
| 5,662,108 A | 9/1997 | Budd et al. | |
| 5,697,377 A * | 12/1997 | Wittkampf | 600/374 |
| 5,983,126 A * | 11/1999 | Wittkampf | 600/509 |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |

* cited by examiner

*Primary Examiner* — Lee S Cohen
(74) *Attorney, Agent, or Firm* — Wiley Rein LLP (57) ABSTRACT

A cardiac navigation system including a mapping catheter, a control system coupled to the mapping catheter, an electrode array, and means for driving an electrical current across the electrode array. The mapping catheter includes means for sensing an electrical field. The control system includes means for receiving sensed signals from the mapping catheter. The cardiac navigation system includes at least one electrode array including means for providing an electrical field across three axes. The three axes are approximately orthogonal with respect to one another. The means for driving an electrical current across the three axes includes means for providing a plurality of individual current sources to the electrode array. As such, the cardiac navigation system presented provides a more uniform sheet of current across an area of interest, the mapping catheter senses the electrical field across the area of interest, and the control system determines a three-dimensional location of the mapping catheter based on the sensed electrical field.

19 Claims, 10 Drawing Sheets

CARDIAC NAVIGATION SYSTEM INCLUDING ELECTRODE ARRAY FOR USE THEREWITH

CROSS-REFERENCE TO RELATED APPLICATIONS

The following co-pending application is incorporated by reference as though fully set forth herein: U.S. application Ser. No. 11/647,305, filed 29 Dec. 2009.

BACKGROUND OF THE INVENTION

1. Field of the Invention

The present invention relates to cardiac navigation technology. More specifically, the present invention relates to a cardiac navigation system including an electrode array for use therewith.

2. Background Art

Cardiac navigation systems are available to provide a means for a physician to locate a site within the heart of a patient for purposes of performing procedures such as tissue ablation. One type of cardiac navigation system includes a cardiac mapping catheter, and a series of active point electrodes disposed on the patient's skin along three approximately orthogonal axes. The cardiac mapping catheter is inserted into a heart chamber of the patient. The active electrodes are then activated to impose an electrical field across the three axes. Such electrical field is then detected by sensing electrodes on the cardiac mapping catheter. The sensing electrodes are then able to take electrophysiological and geometrical measurements, which are used to create an internal map of the heart chamber. Exemplary cardiac navigation systems are disclosed in U.S. Pat. Nos. 5,553,611, 5,662,108, 5,697,377, 5,983,126, 6,728,562, 6,939,309, 6,947,785, and 6,990,370, the disclosures of which are hereby incorporated in their entirety herein, by reference thereto.

One problem with current cardiac navigation systems, however, is their three-dimensional accuracy. For example, although the determination of the location of the catheter is relatively reliable for the purpose of marking a specific site, and thus facilitating return to that site, such systems do not always provide a sufficiently accurate three-dimensional surface model of the heart chamber. Specifically, "location distortion," caused by inherent limitations in cardiac navigation systems, results in surface model distortions.

Moreover, comparison between the resulting surface model and high resolution images of the heart chamber, such as those obtained from Ultrasound, CT or MRI scans, do not match. Location distortion is the result of two primary factors: 1) irregular conductivity of the body tissue; and 2) inconsistencies in current driven across the three approximately orthogonal axes.

The ideal cardiac navigation system would drive a uniform current through a conductive volume of uniform conductivity across each axis. However, the human body does not present a uniform conductivity. A person's blood, heart tissue, lungs, muscle, etc., all have different conductivity. Secondly, current navigation systems fail to create a uniform sheet of current across each axis. Instead, relatively small electrodes are used to drive currents across each axis. In addition, it is known from the construction of such electrodes that more current emanates from the center of the electrode, where the wires that carry the current fan-out, than from the edges and corners.

BRIEF SUMMARY OF THE INVENTION

It is thus desirable to provide a cardiac mapping and navigation system (hereinafter "navigation system") that provides a more uniform sheet of current across three approximately orthogonal axes to more accurately map the chamber of the heart.

Presented herein is a cardiac mapping and navigation system. The cardiac navigation system includes a mapping catheter, a control system coupled to the mapping catheter, an electrode array, and means for driving an electrical current across the electrode array. The mapping catheter includes means for sensing an electrical field. The control system includes means for receiving sensed signals from the mapping catheter. The cardiac navigation system includes at least one electrode array including means for providing an electrical field across multiple axes. The multiple axes are approximately orthogonal with respect to one another. The means for driving an electrical current across the multiple axes includes means for providing a plurality of individual current sources to the electrode array. As such, the cardiac navigation system presented provides a more uniform sheet of current across an area of interest, the mapping catheter senses the electrical field across the area of interest, and the control system determines a three-dimensional location of the mapping catheter based on the sensed electrical field.

Also presented herein are alternative embodiments of a cardiac navigation system, alternative embodiments of an electrode array for use in any of the described cardiac navigation systems, and methods of mapping a chamber of a heart of a patient.

BRIEF DESCRIPTION OF THE DRAWINGS

The accompanying figures, which are incorporated herein and form part of the specification, illustrate a cardiac navigation system and electrode array for use therewith. Together with the description, the figures further serve to explain the principles of the cardiac navigation system and electrode array described herein, and thereby enable a person skilled in the pertinent art to make and use the cardiac navigation system and electrode array.

DETAILED DESCRIPTION OF THE INVENTION

A cardiac navigation system and electrode array, in accordance with the present invention, are described below with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the appended claims.

Figure 1A:
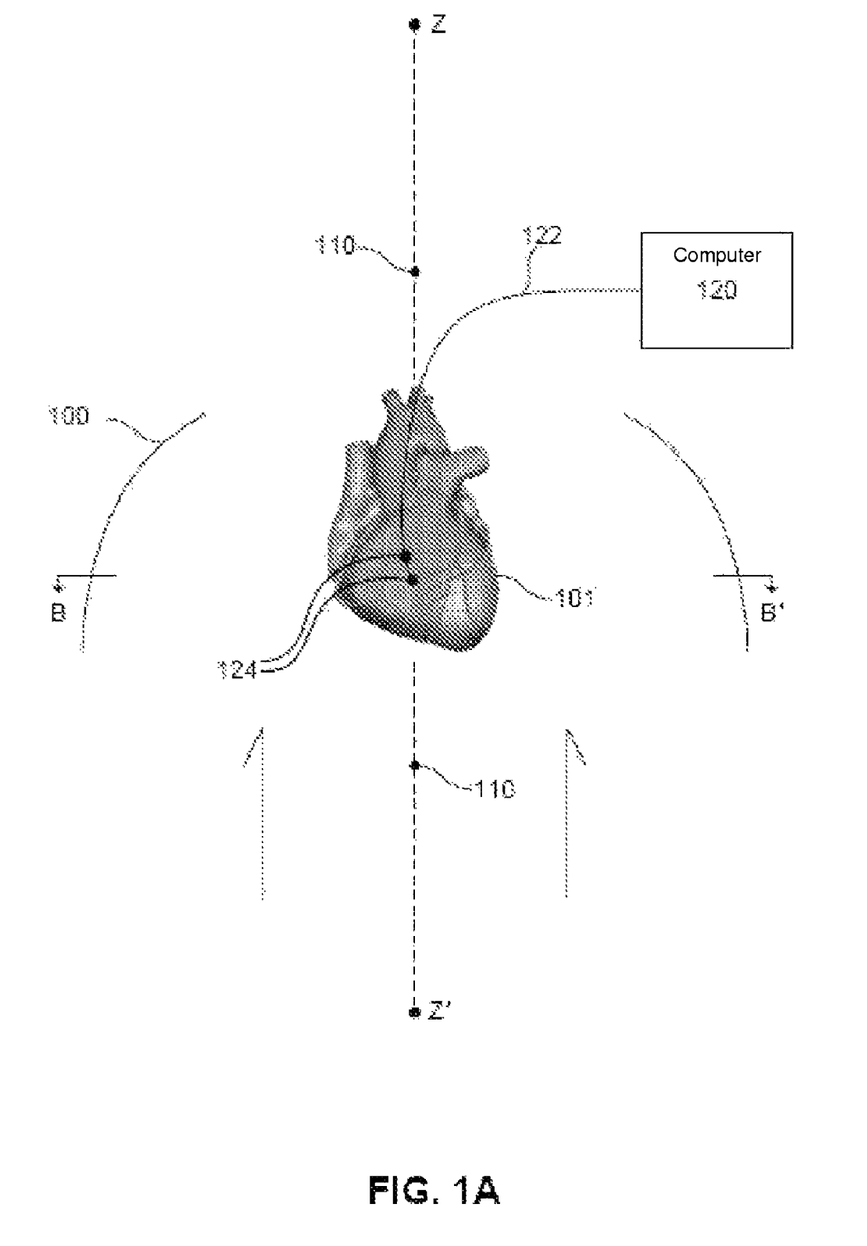
FIG. 1A is a schematic view of a cardiac navigation system.
Figure 1B:
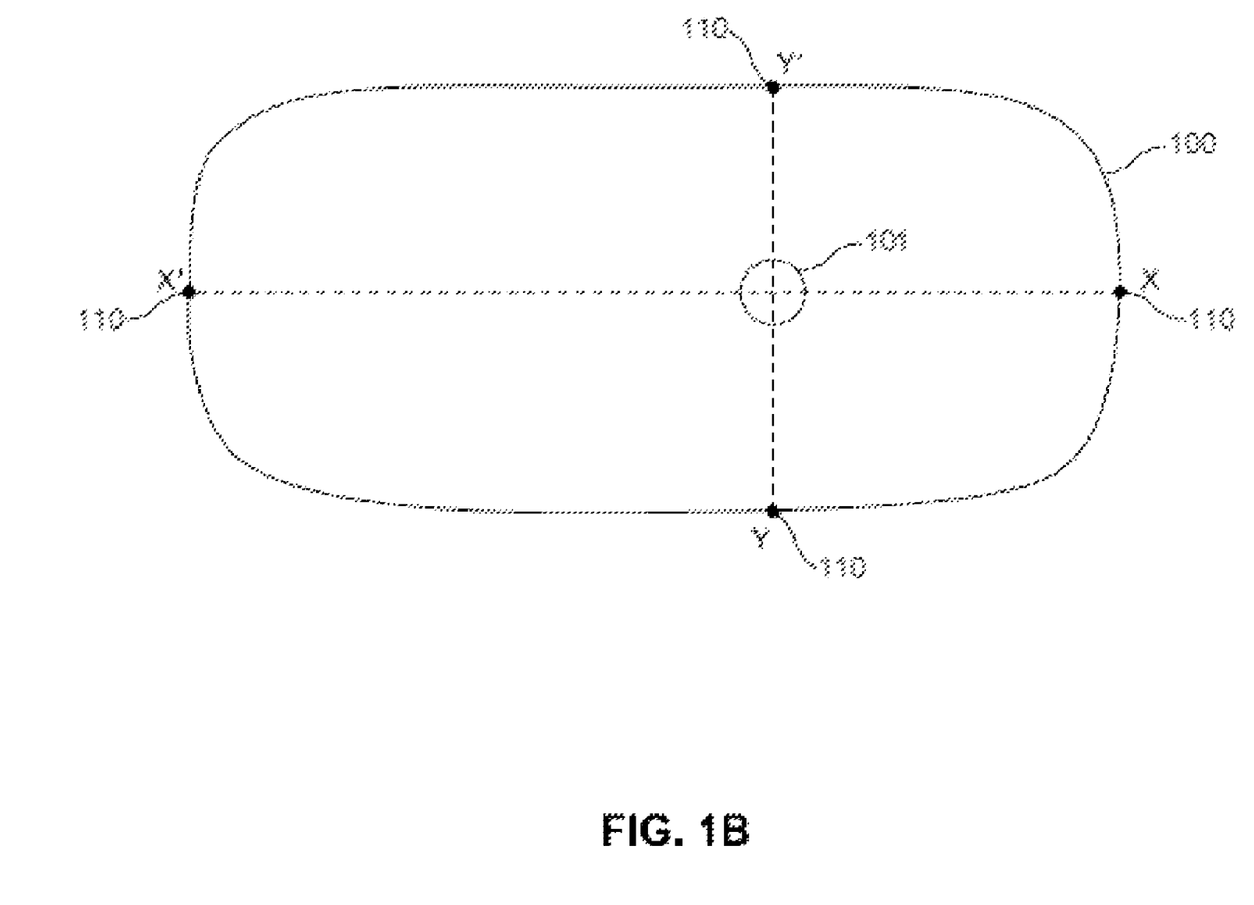
FIG. 1B is a perspective view taken along line B-B' of FIG. 1A.

FIG. 1A shows a schematic view of a cardiac navigation system. FIG. 1B shows a cross-sectional view taken along line B-B' of FIG. 1A. A cardiac mapping catheter 122 is inserted into a patient 100 such that the distal end of the catheter is within a chamber of the patient's heart 101. Cardiac mapping catheter 122 includes two cardiac mapping electrodes 124. Alternative embodiments of cardiac mapping catheter 122 may include any number of cardiac mapping electrodes deemed necessary by one of skill in the art. Cardiac mapping electrodes 122 are typically passive sensing electrodes for sensing an electrical field in the area of interest. Cardiac mapping catheter 122 is electrically coupled to a control system, such as computer system 120.

Electrodes 110 are positioned on the patient's 100 body along three approximately orthogonal axes X, Y, and Z. Previous cardiac navigation systems, for example the system disclosed in U.S. Pat. Nos. 5,697,377 and 5,983,126, include two point electrodes 110, one each on opposite sides of a particular axis. Electrodes 110 are generally adapted to deliver current pulses through the patient's body. As such, electrodes 110 can deliver current pulses directed along the three approximately orthogonal axes X, Y, and/or Z. When transmitted through the patient's body, these pulses or voltages are ultimately sensed by cardiac navigation electrodes 124 of the cardiac mapping catheter 122. The communication between electrodes 110 and cardiac mapping catheter 122 provides a positioning system, which allows computer system 120 to generate a three-dimensional map of the inner chamber of the heart 101 of patient 100. Specifically, computer system 120 can determine a three-dimensional point, providing a location of the cardiac mapping catheter 122, from the information sensed by cardiac navigation electrodes 124. Such determination is based on the fact that the measured potential is a function of the location of the cardiac navigation electrodes. Such a navigation system may be used to create a computerized three-dimensional map of the internal chambers of the patient's heart 101.

As discussed above, however, previous cardiac navigation systems may produce distorted three-dimensional diagrams due in part to limitations with the electrodes used in such navigation systems. To address the issue of distortion, an electrode array has been developed, and is presented herein, to replace the electrodes 110 of previous navigation systems. In one embodiment, an array of surface electrodes is presented. In an alternative embodiment, a patch electrode is presented.

Figure 1C:
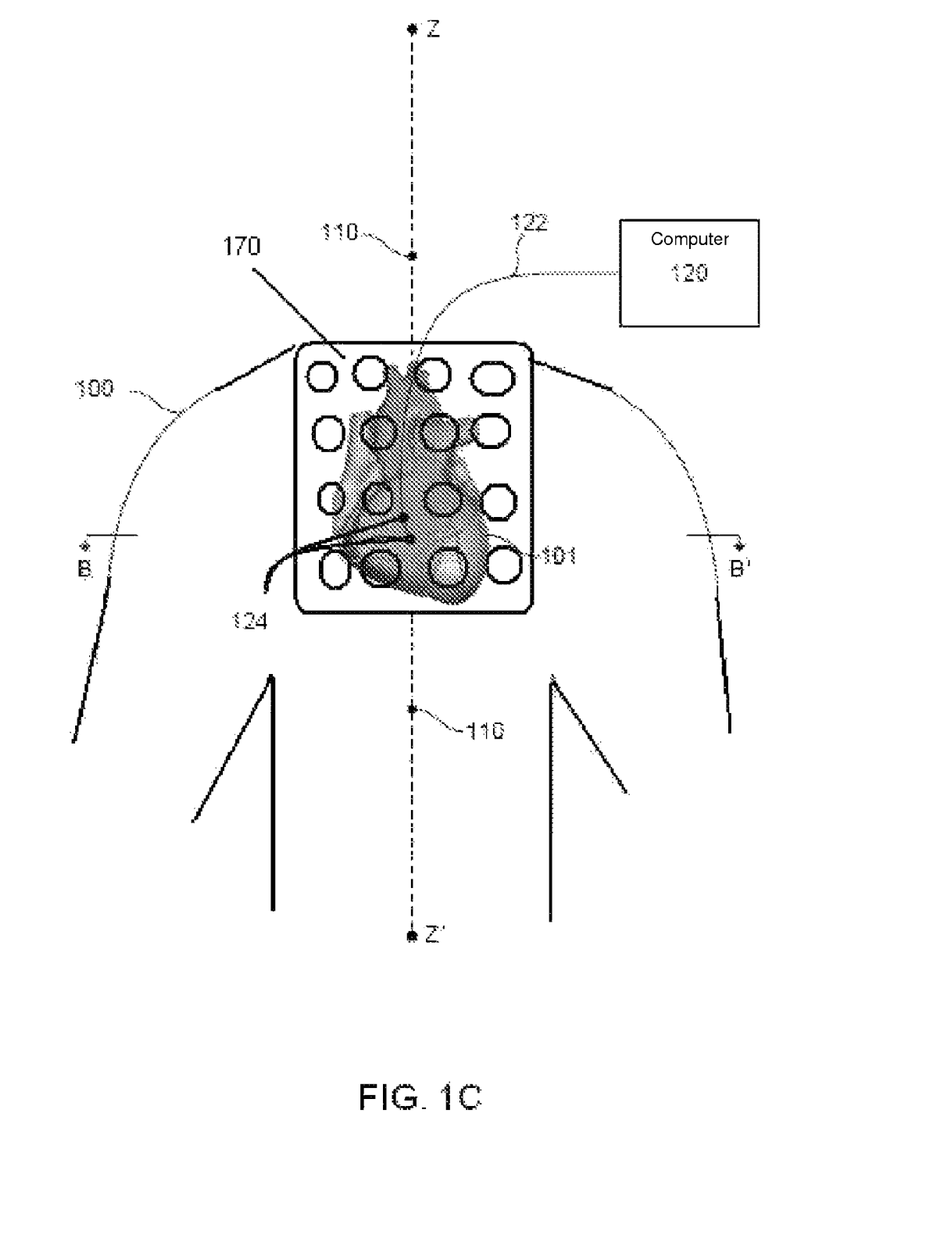
FIG. 1C is a schematic view of a cardiac navigation system in accordance with one embodiment of the present invention.
Figure 1D:
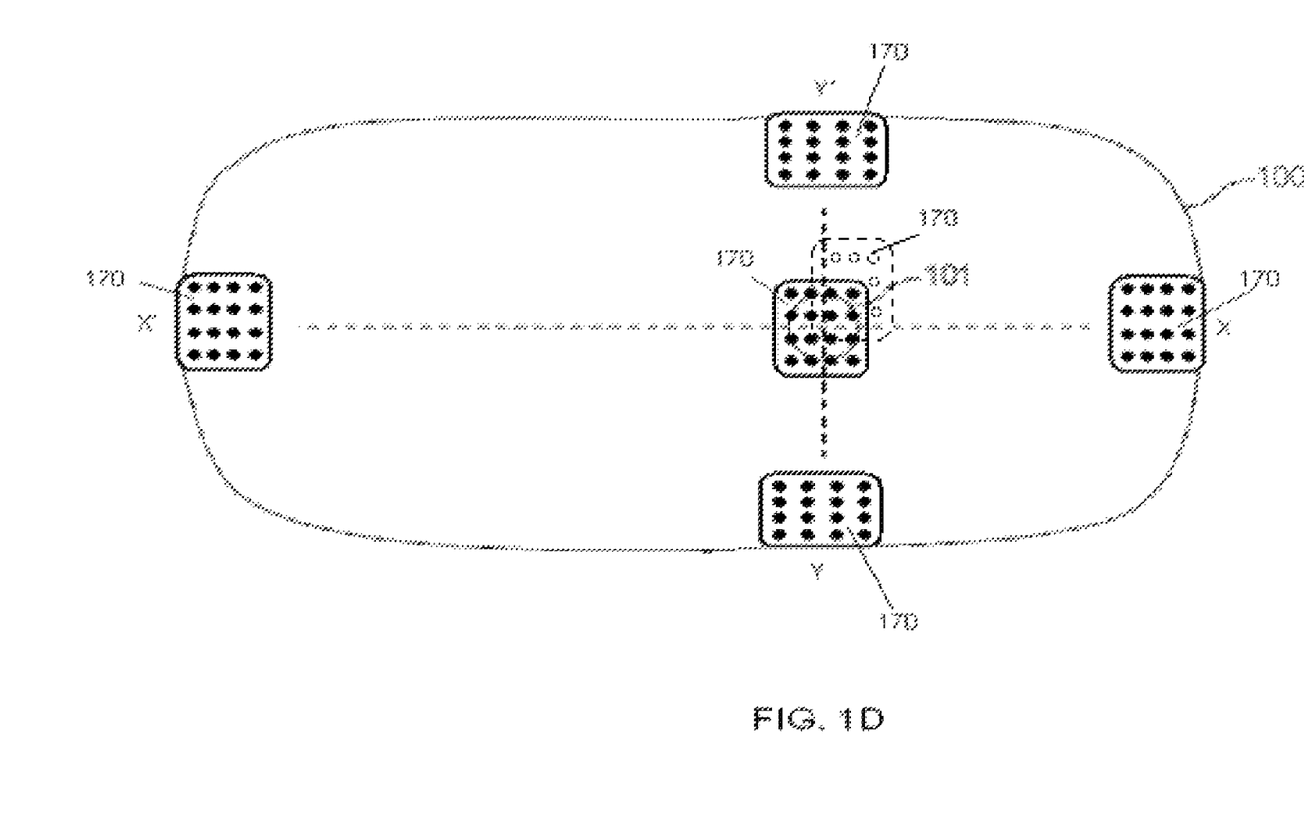
FIG. 1D is a perspective view taken along line D-D' of FIG. 1C.

FIG. 1C shows a schematic view of a cardiac navigation system including an array of surface electrodes. FIG. 1D shows a cross-sectional view taken along line B-B' of FIG. 1C. As discussed above, a cardiac mapping catheter 122 is inserted into patient 100 such that the distal end of the catheter is within a chamber of the patient's heart 101. Cardiac mapping catheter 122 includes two cardiac mapping electrodes 124. Alternative embodiments of cardiac mapping catheter 122 may include any number of cardiac mapping electrodes deemed necessary by one of skill in the art. Cardiac mapping electrodes 122 are typically passive sensing electrodes for sensing an electrical field in the area of interest. The cardiac mapping electrodes can also be dual use electrodes, for example, serving both ablation and sensing roles. A cardiac mapping catheter 122 may also include a special element for sensing or varying in response to a magnetic field or electromagnetic field. Cardiac mapping catheter 122 is electrically coupled to a control system, such as computer system 120.

In the embodiment shown in FIGS. 1C and 1D, the electrodes 110 of FIGS. 1A and 1B are replaced with an electrode array; and more specifically with an array of surface electrodes 170. As used herein, the term "array" is intended to broadly define an "orderly or intentional arrangement." Further, the term "electrode array" is intended to broadly define an "orderly or intentional arrangement of source/sink points." In other words, an "electrode" should be interpreted to mean any component that is able to act as a source or a sink of an electrical current and/or voltage. An "electrode" should not be limited to the surface electrodes shown in the array of surface electrodes 170 shown in FIGS. 1C and 1D. Instead, the term "electrode" in "electrode array" should be interpreted broadly enough to include such components as the individual conductive contact points of the patch electrodes discussed below.

As shown in one example, array 170 includes sixteen surface electrodes, specifically a four-by-four array of electrodes Alternatively, any number of surface electrodes may be employed. Array 170 is positioned on the body of patient 100 along multiple, e.g., three approximately orthogonal axes X, Y, and Z. Array 170 includes a plurality of electrodes generally adapted to deliver or receive current pulses transmitted through the patient's body. As such, array 170 can deliver an array of current or voltage pulses directed along the approximately orthogonal axes X, Y, and/or Z. In operation, one array 170 acts as the current or voltage source while the corresponding array 170 (not shown) acts as the current or voltage sink. The current or voltage pulses transmitted by array 170 thereby create a uniform electrical field that can be detected by the cardiac mapping electrodes 124 of the cardiac mapping catheter 122.

The communication between the array of electrodes 170 and cardiac mapping catheter 122 provides a positioning system, which allows computer system 120 to generate a three-dimensional map of the inner chamber of the heart 101 of patient 100. Specifically, computer system 120 can determine a three-dimensional point, providing a location of the cardiac mapping catheter 122, from the information sensed by cardiac mapping electrodes 124. Such determination is based on the fact that the measured potential is a function of the location of the cardiac mapping electrodes. Such a navigation system may be used to create a computerized three-dimensional diagram of the internal chambers of the patient's heart 101. The uniformity of the electrical field provided by the array of surface electrodes 170 address the issue of geometric distortion previously observed by other cardiac navigation systems.

In an alternative embodiment, a patch electrode is presented. The patch electrode includes an array of conductive contact points which serve as current sources/sinks that deliver a plurality of individual current pulses/voltages. The cumulative effect of these conductive contact points is a more homogenous potential field delivered across the region of interest. Such patch electrode may be used in lieu of the array of surface electrodes 170 shown in FIGS. 1C and 1D.

Figure 2:
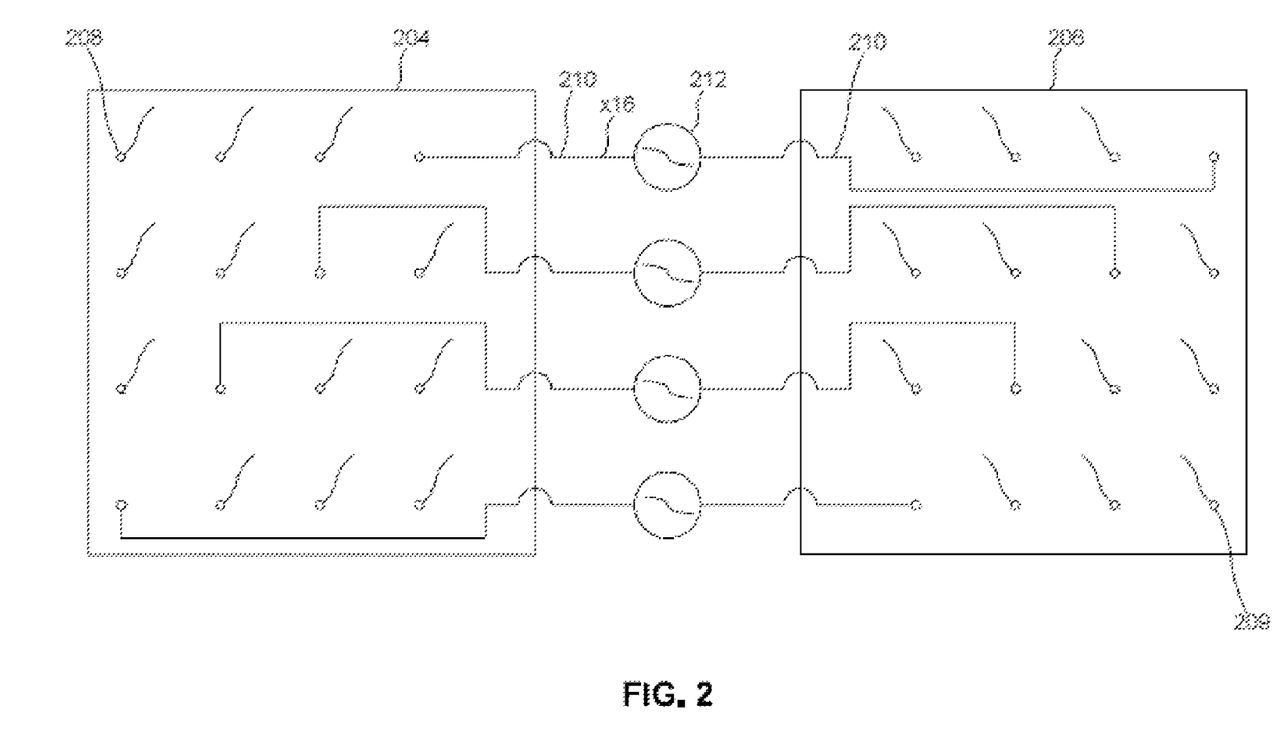
FIG. 2 is a schematic view of a patch electrode in accordance with one embodiment of the present invention.

FIG. 2 shows a schematic view of one such patch electrode. Patch array 204, and corresponding patch array 206, are forward and backward patch arrays, respectively. Each array includes a plurality of electrodes, or contact points 208, 209. As shown, each patch array 204, 206 includes sixteen contact points 208, 209. Although sixteen are shown, any number of contact points may be employed. Ideally, the contact points are of sufficient number, size, and spacing, so as to create a uniform electrical field over the target tissue. Contact points 208, 209 are preferably arranged in a uniform array; for example, a four-by-four array, as shown, but can be arranged in any pattern that provides a uniform electrical field. The overall size of the array is significantly larger than the point electrodes 110 used in modern cardiac navigation systems. This increased size allows the array to provide a more uniform electrical field. As such, the array of individual contact points 208, 209 serve as means for providing a uniform electrical field across an axis.

Each contact point 208 on patch array 204 is electrically coupled to a corresponding contact point 209 on patch array 206. The electrodes may be coupled via a conductive wire 210 or other means known in the art. Disposed along the electrical path of each conductive wire 210 is an individual current source 212. For simplicity, only four such electrical connections are displayed. However, one of skill in the art would readily appreciate that the shown couplings are repeated for the number of corresponding contact points 208. This provides electrical flow between contact points 208 on patch array 204 and contact points 209 on patch array 206. More specifically, each contact point 208, 209 is electrically coupled to an individual current source 212 to thereby provide sixteen individual current loops.

Alternatively, contact points 208, 209 may be coupled digitally, or through a non-preset coupling system, such as analog switches. As such, a control system may be established to determine the optical contact point coupling. In particular, the system may digitally, or through the use of analog switches, determine an optimal coupling of a first contact point or electrode on a first side of an axis, e.g., the x axis, with any one of the other electrodes or contact points, typically being an electrode or contact point on a second, or opposite, side of the same axis.

When in operation, each patch array 204, 206 is disposed on the surface of the patient's body. Each contact point 208 serves as an individual current source and each contact point 209 serves as an individual current sink. As such, in the embodiment shown in FIG. 2, sixteen individual current pulses are delivered through the body from patch array 204 to patch array 206. This transmission of multiple current sources provides a more homogeneous electrical field across the body, and specifically across the area of interest in the body.

It should be noted that alternative embodiments may include a preset grid of contact points or surface electrodes, including multiple leads to each contact point or surface electrode. These preset grids may provide electrodes at a known distribution, e.g., with a set distance between each electrode. Alternatively, a flexible grid of adjustable contact points or surface electrodes may be employed. Further, a dynamic coupling system may be employed in which the contact points and/or surface electrodes are adjustably coupled to one another. Such a dynamic coupling system may employ analog switches, digital switches, circuitry to produce differential drive currents amongst the contact points or surface electrodes, and/or a feedback control system to determine what switching and/or drive configuration is most prudent to provide the best results.

Figure 3:
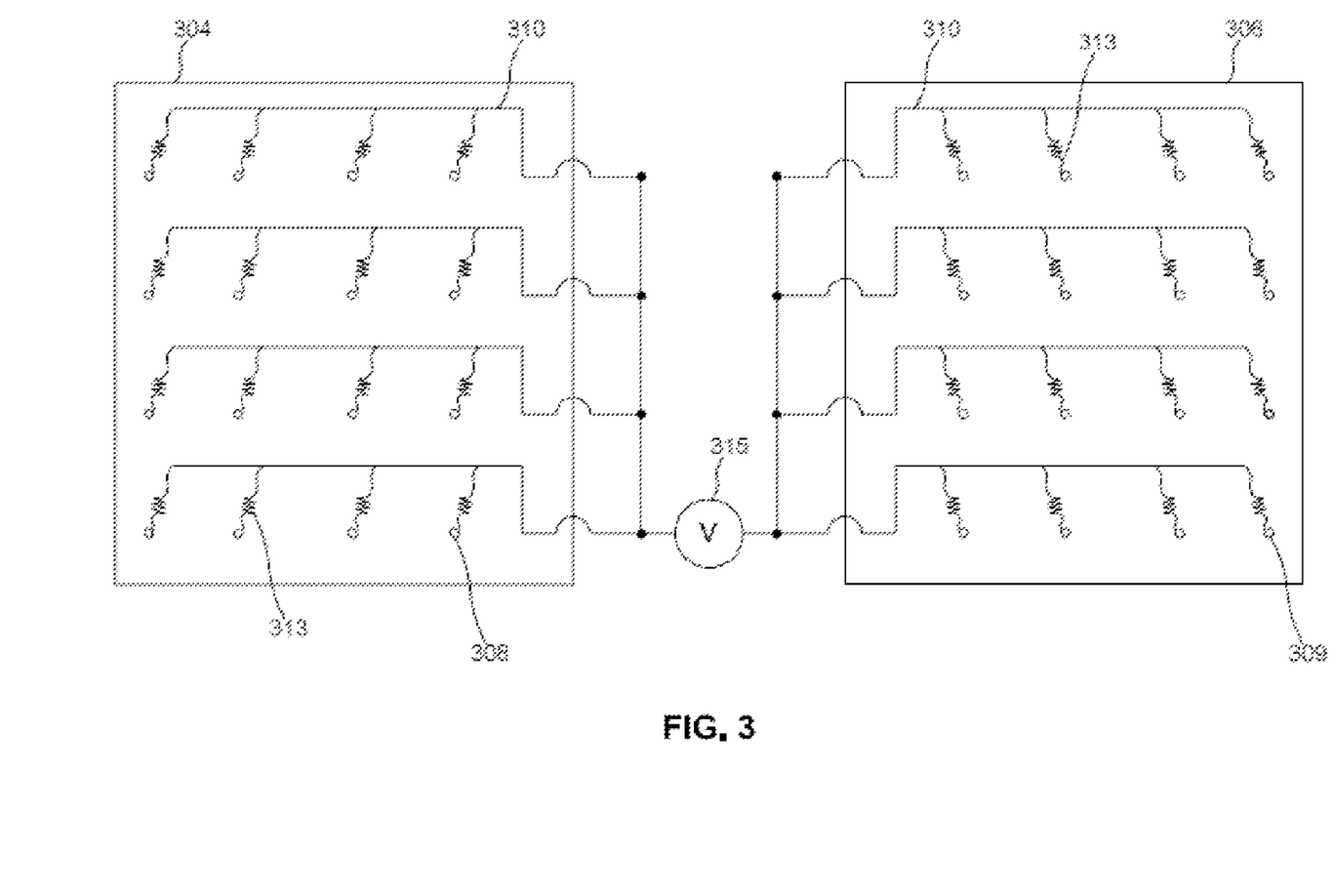
FIG. 3 is a patch electrode in accordance with an alternative embodiment of the present invention.

FIG. 3 shows patch arrays 304, 306. Patch arrays 304, 306 differ from the patch arrays 204, 206 shown in FIG. 2 in that the array of contact points 308, 309 are electrically coupled to a single voltage source 315. Such an alternative connection may be desirable to simplify the circuit design. As shown, each contact point 308 on patch array 304 is coupled to a resistor 313. Similarly, each contact point 309 on patch array 306 is coupled to a resistor 313. Each resistor 313 is coupled at one end to a contact point 308, 309 and coupled at another end to voltage source 315. The plurality of resistors 313 are coupled to a single voltage source 315 via conductive wires 310. Such a configuration provides a uniform delivery of current to each contact point 308, 309. Thus, each contact point 308 serves as an individual current source and each contact point 309 serves as an individual current sink. Resistors 313 are preferably between 5-10 kΩ.

The plurality of individual current sources described in FIG. 2, or the voltage source described in FIG. 3, as well as the associated circuitry, serve as a means for driving an electrical current across an electrode. More specifically, these configurations provide a means for providing a plurality of individual current sources to at least one pair of electrodes.

Figure 4A:
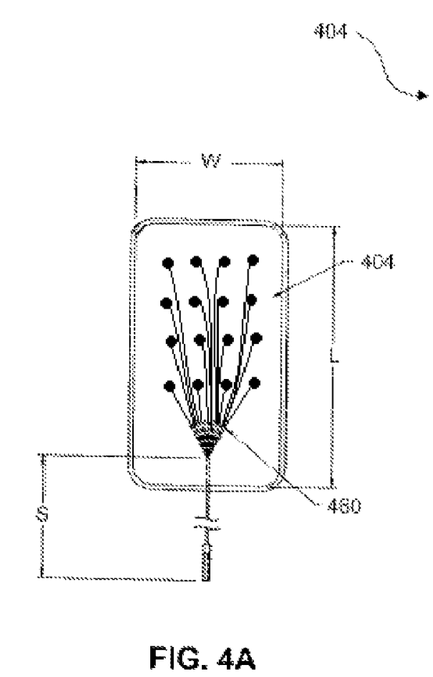
FIG. 4A is a schematic view of a patch electrode in accordance with an alternative embodiment.

FIG. 4A is a schematic view of a patch array 404, in accordance with one embodiment of the present invention. Array 404 generally has a length L of approximately seven inches and a width W of approximately four inches. Array 404 also includes wire leads 460. Wire leads 460 bring individual electrical currents to the individual contact points within patch array 404. The individual wire leads 460 are preferably separated by 0.050 inches.

Figure 4B:
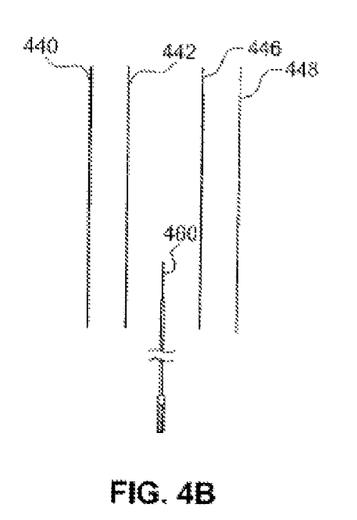
FIG. 4B is an exploded side view of the patch electrode of FIG. 4A.

FIG. 4B is an exploded side view of patch array 404. Patch array 404 is generally formed of a foam base 440. Foam base 440 includes a pressure sensitive adhesive. Patch array 404 also includes a reinforcement film 442, which also includes a pressure sensitive adhesive. Patch array 404 also includes a non-conductive substrate 446, such as a carbon film. Non-conductive substrate 446 is preferably screen printed with a conductive material, such as silver ink, to create the array of contact points discussed above. Each contact point is coupled to an individual lead wire 460 through the non-conductive substrate 446. A layer of conductive gel 448, such as an RG63B gel with a polyester release liner may then be disposed on the non-conductive substrate 446. The layer of conductive gel 448 promotes electrical contact between the electrode and the patient's skin.

Figure 5A:
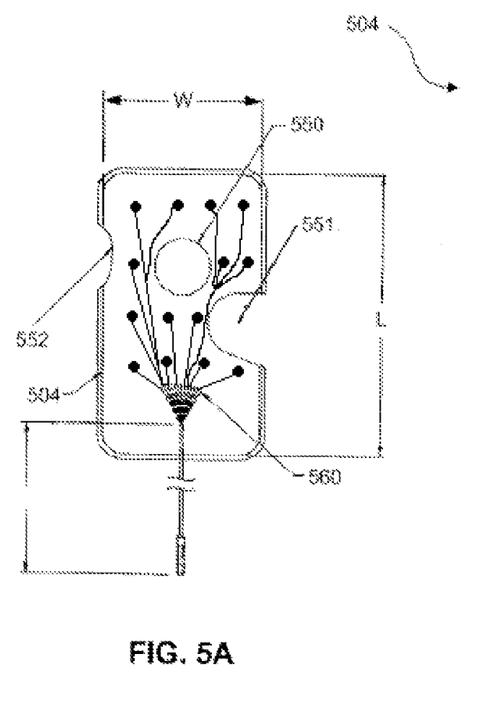
FIG. 5A is a schematic view of a patch electrode in accordance with an alternative embodiment.

FIG. 5A is a schematic view of a an alternative patch array 504. Patch array 504 is similar to patch array 404 of FIG. 4, but differs in that patch array 504 includes openings, or cut-outs, 550, 551, and 552. These openings or cut-outs provide a location for which additional electrodes and/or sensors may be applied. Array 504 generally has a length L of approximately seven inches and a width W of approximately four inches. Array 504 also includes wire leads 560. Wire leads 560 bring individual electrical currents to the individual contact points within patch array 504. The individual wire leads 560 are preferably separated by 0.050 inches.

Figure 5B:
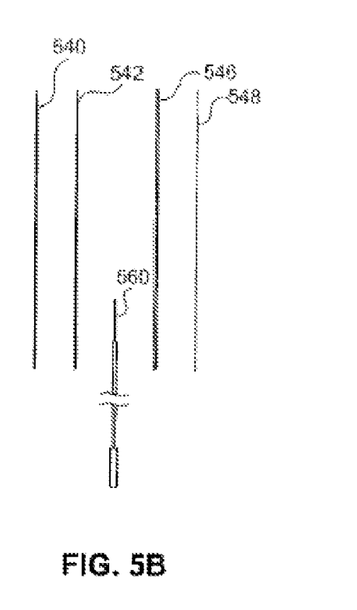
FIG. 5B is an exploded side view of the patch electrode of FIG. 5A.

FIG. 5B is an exploded side view of patch array 504. Patch array 504 is generally formed of a foam base 540. Foam base 540 includes a pressure sensitive adhesive. Patch array 504 also includes a reinforcement film 542, which also includes a pressure sensitive adhesive. Patch array 504 also includes a non-conductive substrate 546, such as a carbon film. Non-conductive substrate 546 is preferably screen printed with a conductive material, such as silver ink, to create the array of contact points discussed above. Each contact point is coupled to an individual lead wire 560 through the non-conductive substrate 546. A layer of conductive gel 548, such as an RG63B gel with a polyester release liner may then be disposed on the non-conductive substrate 546. The layer of conductive gel 548 promotes electrical contact between the electrode and the patient's skin.

Figure 6A:
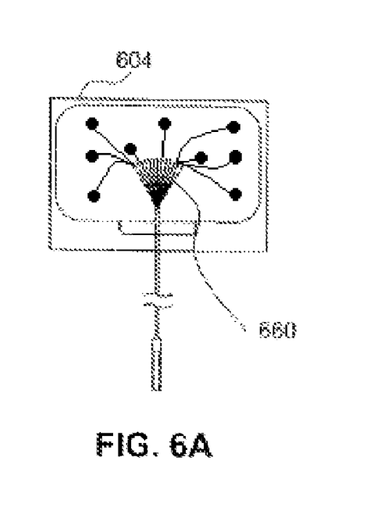
FIG. 6A is a schematic view of a patch electrode in accordance with an alternative embodiment.

Patch array 404 and 504 are preferably used in conjunction with the lateral (left-right) and/or anterior-posterior axes. An alternative patch array 604 is shown in FIG. 6A. Patch array 604 is smaller in size and is more suitable for placement in the arms or legs of the patient.

Figure 6B:
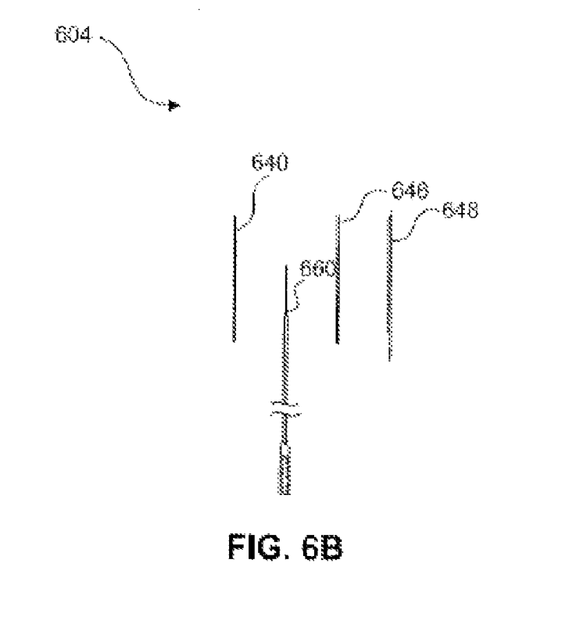
FIG. 6B is an exploded side view of the patch electrode of FIG. 6A.

Array 604 also includes wire leads 660. Wire leads 660 bring individual electrical currents to the individual contact points within patch electrode 604. The individual wire leads 660 are preferably separated by 0.050 inches. FIG. 6B is an exploded side view of patch array 604. Patch array 604 is generally formed of a foam base 640. Foam base 640 includes a pressure sensitive adhesive. Patch array 604 includes a non-conductive substrate 646, such as a carbon film. Non-conductive substrate 646 is preferably screen printed with a conductive material, such as silver ink, to create the array of contact points discussed above. Each contact point is coupled to an individual lead wire 660 through the non-conductive substrate 646. A layer of conductive gel 648, such as an RG63B gel with a polyester release liner may then be disposed on the non-conductive substrate 646. The layer of conductive gel 648 promotes electrical contact between the electrode and the patient's skin.

Figure 7:
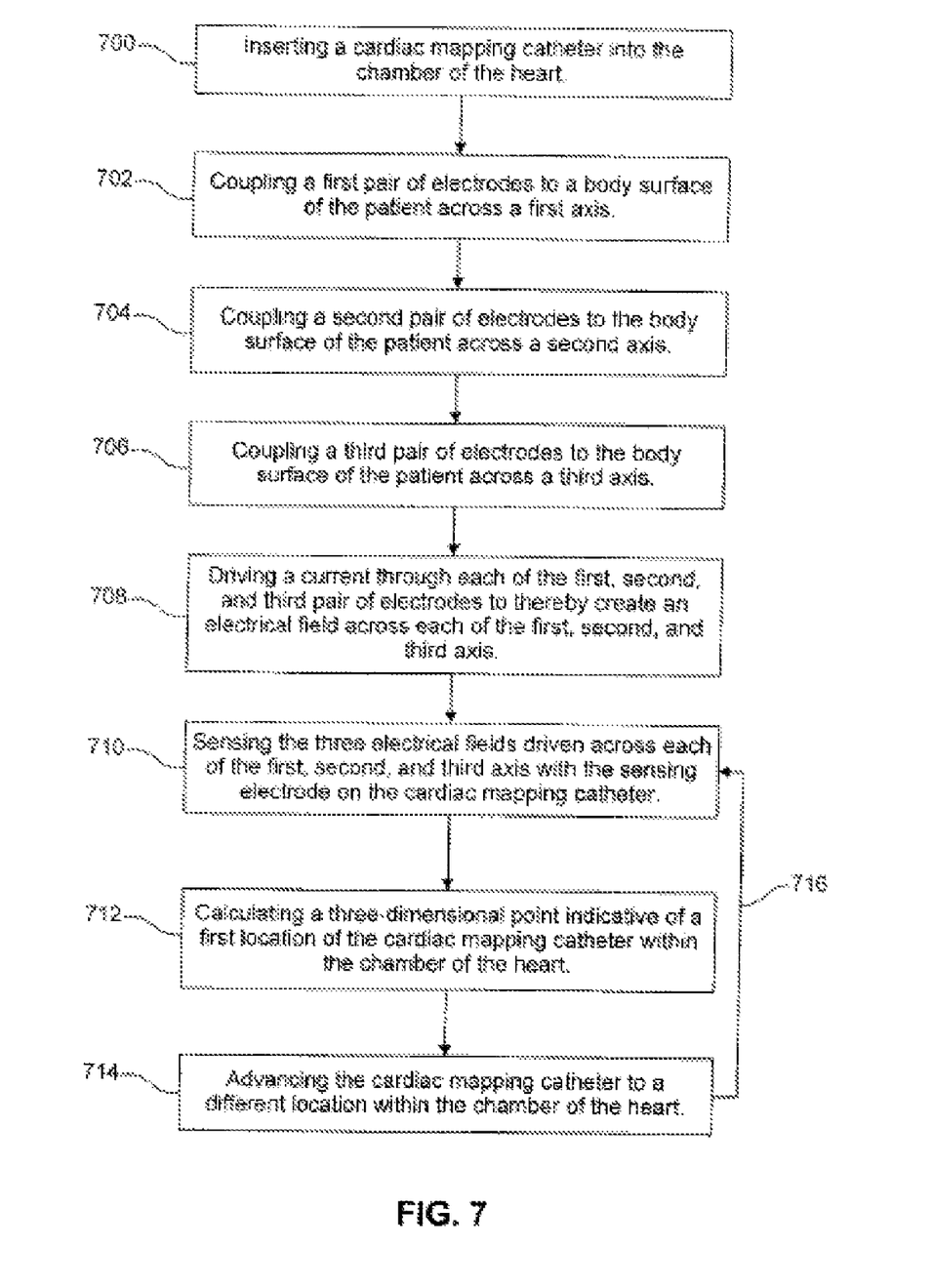
FIG. 7 is a flow-chart depicting a method of mapping a chamber of a heart of a patient.

FIG. 7 is a flow-chart depicting a method of navigation a chamber of a heart of a patient. In step 700, a cardiac mapping catheter is inserted into a chamber of a patient's heart. The cardiac mapping catheter includes at least one sensing electrode. In steps 702-706, first, second, and third pairs of electrodes are coupled to the body surface of the patient across first, second, and third axes, respectively. The first, second, and third axis are approximately orthogonal with respect to one another. In one embodiment, the electrodes are any one of the patch electrodes described above. In an alternative embodiment, an array of surface electrodes are coupled to the body surface as described in FIGS. 1C and 1D. If patch arrays are used, each conductive contact point in the array of contact points serves as an individual source or sink of current. Alternatively, if an array of surface electrodes is used, each surface electrode serves as an individual source or sink of current.

In step 708, a current is driven through each of the first, second, and third pair of electrodes to thereby create an electrical field across each of the first, second, and third axis. If patch arrays are used, step 708 includes driving an individual current through each of the individual conductive contact points in patch electrode. If an array of surface electrodes is used, step 708 includes driving an individual current through each of the individual surface electrodes. In step 710, the three electrical fields are sensed across each of the first, second, and third axis with the sensing electrode on the cardiac mapping catheter. In step 712 a three-dimensional point indicative of a first location of the cardiac mapping catheter within the chamber of the heart is calculated. In step 714, the cardiac mapping catheter is advanced to a second location within the chamber of the heart. Arrow 716 indicates that steps 710-714 are repeated to determine a second three-dimensional point indicative of a second location of the cardiac mapping catheter within the chamber of the heart. These steps are repeated until a full map of the internal chamber is created.

In one embodiment, step 708 includes driving individual currents at varying time intervals. For example, at Time1, pulses can be delivered through the electrodes positioned along the X axis. At Time2, pulses can be delivered through the electrodes positioned along the Y axis. At Time3, pulses can be delivered through the electrodes positioned along the Z axis. This system provides a distinguishing feature such that the sensing electrode on the cardiac mapping catheter can differentiate between an electrical field in the X, Y, or Z direction. In another embodiment, the pulses or electrical fields may be distinguished by varying frequencies. For example, pulses delivered through the electrodes positioned along the X axis can be delivered at one frequency while pulses delivered through the electrodes positioned along the Y axis and the Z axis can be delivered at second and third frequencies, respectively. In another embodiment, a combination of time variation and frequency variation may be employed to distinguish between electrical fields created in the X, Y, or Z direction. Similar means of distinguishing, or separating, the X, Y, and Z electrical fields are described in, for example, U.S. Pat. No. 5,697,377, which has been incorporated herein by reference. In yet another embodiment, time variation and/or frequency variation may be employed between electrodes or contact points within a given array. For example, an array of surface electrodes positioned along an axis can deliver pulses at varying times or frequencies in order to adjust the uniformity of the electrical field delivered across the axis.

The system presented herein is also useful in conjunction with other imaging and navigation systems. For example, the cardiac navigation system presented herein can be used with digital image fusion systems. Such systems may combine one or more images from instruments such as Ultrasound, MRI, and/or CT scans to produce a dynamic high resolution model. An exemplary system is described in U.S. Pat. No. 6,556,695, which is incorporated herein, in its entirety, by reference thereto.

What has been proposed herein is an array of surface electrodes and a patch including an array of individual contact points serving as individual current sources and/or sinks. In this way, variations in electrode-skin impedance are overcome, and a much more uniform sheet of current is sourced and sunk across the patient's body. While various embodiments of a cardiac navigation system have been described, it should be understood that they have been presented by way of example, and not limitation. For example, the design, shape, and size of the patch electrode may vary. Further, the number and configuration of the array of surface electrodes may vary. It will be apparent to a person skilled in the relevant art that various changes in form and detail can be made therein without departing from the spirit and scope of the appended claims. Thus the present invention should not be limited by any of the above-described exemplary embodiments, but should be defined only in accordance with the following claims and their equivalents. Further, the Abstract and Brief Summary of the Invention sections are not intended to be limiting, but are only intended to summarize the description presented herein.

What is claimed is:

1. A cardiac navigation system comprising:
    a mapping catheter including at least one sensing electrode;
    a plurality of individual current sources;
    a first array having,
        a first non-conductive substrate,
        a first plurality of conductive contact points disposed about the first non-conductive substrate;
    a second array having,
        a second non-conductive substrate,
        a second plurality of conductive contact points disposed about the second non-conductive substrate;
    a first plurality of conductive leads electrically connected between respective ones of the plurality of individual current sources and respective ones of the first plurality of conductive contact points; and
    a second plurality of conductive leads electrically connected between respective ones of the plurality of individual current sources and respective ones of the second plurality of conductive contact points, wherein the at least one sensing electrode of the mapping catheter is configured to sense an electrical field generated by the first and second arrays.

2. The cardiac navigation system of claim 1, wherein each array includes at least nine conductive contact points.

3. The cardiac navigation system of claim 2, wherein each array includes at least sixteen conductive contact points.

4. The cardiac navigation system of claim 1, wherein the first and second plurality of conductive contact points are screen printed onto the first and second non-conductive substrate, respectively.

5. The cardiac navigation system of claim 1, wherein the first and second non-conductive substrates are comprised of carbon film.

6. The cardiac navigation system of claim 5, wherein the first and second plurality of conductive contact points are formed of silver ink applied to the carbon film.

7. The cardiac navigation system of claim 1, wherein the first plurality of conductive leads are connected between one, and only one, individual current source and one, and only one, of the first plurality of contact points.

8. The cardiac navigation system of claim 1, wherein the first array is at least 3 inches wide and 3 inches long.

9. The cardiac navigation system of claim 8, wherein the first array is at least 6 inches wide and 4 inches long.

10. The cardiac navigation system of claim 1, wherein the plurality of conductive contact points for each array are arranged in a uniformly distributed array.

11. The cardiac navigation system of claim 1, wherein the first non-conductive substrate is attached to the second non-conductive substrate.

12. A cardiac navigation system comprising:
a mapping catheter;
a control system adapted for coupling to the mapping catheter and including means for receiving sensed signals from the mapping catheter;
a first array having means for providing a first electrical field across a first axis;
a second array having means for providing a second electrical field across a second axis;
a third array having means for providing a third electrical field across a third axis; and
means for driving an electrical current across the first, second, and third array, wherein said means for driving an electrical current across the first, second, and third array includes means for providing a plurality of distinct current sources to at least one of the first, second, or third electrode array;
wherein the first, second, and third electrode array provide approximately orthogonal electrical fields across an area of interest.

13. The cardiac navigation system of claim 12, wherein at least one of the first, second, or third array comprises a plurality of surface electrodes.

14. The cardiac navigation system of claim 12, wherein at least one of the first, second, or third array comprises a patch electrode having a non-conductive substrate, and a plurality of conductive contact points disposed about the non-conductive substrate.

15. The cardiac navigation system of claim 14, wherein a resistor is coupled between each of the plurality of conductive contact points and a current source.

16. The cardiac navigation system of claim 12, wherein at least one of the first, second, or third array comprises a plurality of independent current sources.

17. A method of mapping a chamber of a heart of a patient comprising:
(a) inserting a cardiac mapping catheter into the chamber of the heart, wherein the cardiac mapping catheter includes at least one sensing electrode;
(b) coupling a first array to a body surface of the patient across a first axis;
(c) coupling a second array to the body surface of the patient across a second axis;
(d) coupling a third array to the body surface of the patient across a third axis; wherein the first, second, and third axis are approximately orthogonal with respect to one another, and wherein at least one of the first, second, or third array includes a plurality of individual current source points;
(e) driving a current through each of the first, second, and third arrays to thereby create an electrical field across each of the first, second, and third axis; wherein the driving step includes driving an individual current through each of the individual current source points;
(f) sensing the three electrical fields across each of the first, second, and third axis with the sensing electrode on the cardiac mapping catheter;
(g) determining a three-dimensional point indicative of a first location of the cardiac mapping catheter within the chamber of the heart;
(h) advancing the cardiac mapping catheter to a second location within the chamber of the heart; and
repeating steps (f) and (g) to determine a second three-dimensional point indicative of a second location of the cardiac mapping catheter within the chamber of the heart.

18. The method of claim 17, wherein step (e) comprises driving a current through each of the first, second, and third arrays in time sequence.

19. The method of claim 17, wherein step (e) comprises driving a current through each of the first, second, and third arrays at respectively different frequencies.

* * * * *